(12) United States Patent
Durando et al.

(10) Patent No.: US 6,338,276 B1
(45) Date of Patent: Jan. 15, 2002

(54) MULTIPHASE FLOW METERING METHOD AND DEVICE

(75) Inventors: Pierre Durando, Lyons; Yvon Castel, Croissy sur Seine; Daniel Ferre, Sautron; Jean Falcimaigne, Bois Colombes; Eric Vandenbroucke, Rueil-Malmaison, all of (FR)

(73) Assignee: Institut Francais du Petrole, Ruiel Malmaison Cedex (FR)

( * ) Notice: Subject to any disclaimer, the term of this patent is extended or adjusted under 35 U.S.C. 154(b) by 0 days.

(21) Appl. No.: 09/218,039

(22) Filed: Dec. 22, 1998

(30) Foreign Application Priority Data

Dec. 22, 1997 (FR) .............................. 97 16274

(51) Int. Cl.⁷ .......................... G01F 1/74; G01N 11/00
(52) U.S. Cl. ..................... 73/861.04; 73/200; 73/61.73
(58) Field of Search ............................ 73/861.04, 195, 73/200, 61.44, 61.73

(56) References Cited

U.S. PATENT DOCUMENTS

| | | | |
|---|---|---|---|
| 4,813,270 A | * | 3/1989 | Baillie ...................... 73/861.04 |
| 5,211,842 A | * | 5/1993 | Tuss et al. ............... 73/861.04 |
| 5,393,202 A | | 2/1995 | Levallois ..................... 417/19 |
| 5,494,067 A | | 2/1996 | Levallois .................... 137/154 |
| 5,793,216 A | | 8/1998 | Constant ..................... 324/639 |
| 5,841,020 A | * | 11/1998 | Guelich ................... 73/861.04 |

FOREIGN PATENT DOCUMENTS

| | | | |
|---|---|---|---|
| EP | 0674249 | 4/1990 | .......... G05D/11/00 |
| GB | 2089049 | 6/1982 | |
| WO | 9013859 | 11/1990 | |
| WO | 9526494 | 10/1995 | |

* cited by examiner

*Primary Examiner*—Harshad Patel
(74) *Attorney, Agent, or Firm*—Antonelli, Terry, Stout & Kraus, LLP

(57) ABSTRACT

The invention si a multiphase flow metering method. The method includes a) determining at least two pressure values $P_1$ and $P_2$ for the different points A and B, and the value of the internal pressure Po of a device; and b) determining, from the values determined in step a) from the knowledge of the density of the gas phase and of the liquid phase and/or of the average value of the density of the multiphase medium in a slotted tube, from a relation connecting at least the following parameters: the level of the interface between the liquid phase and the gas phase and/or the volume ratio of the gas phase to the liquid phase (GLR) from pressure values $P_1$, P2, Po, the total flow rate value Qt of the flowing multiphase medium and/or the flow rate $q_g$, $q_1$ of each of the phases.

31 Claims, 2 Drawing Sheets

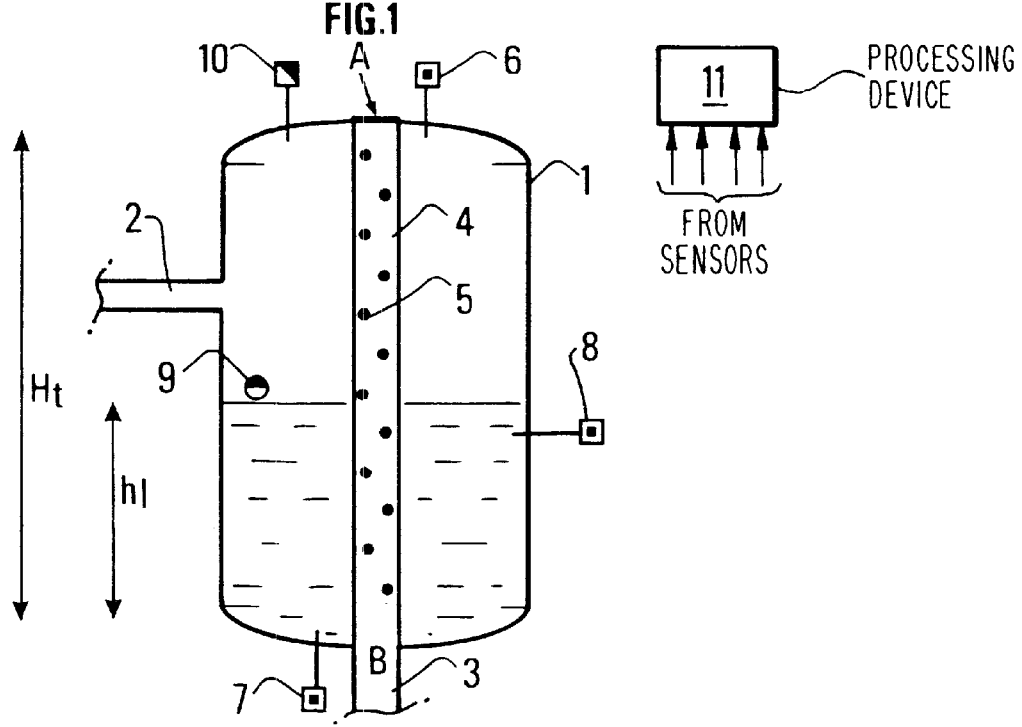
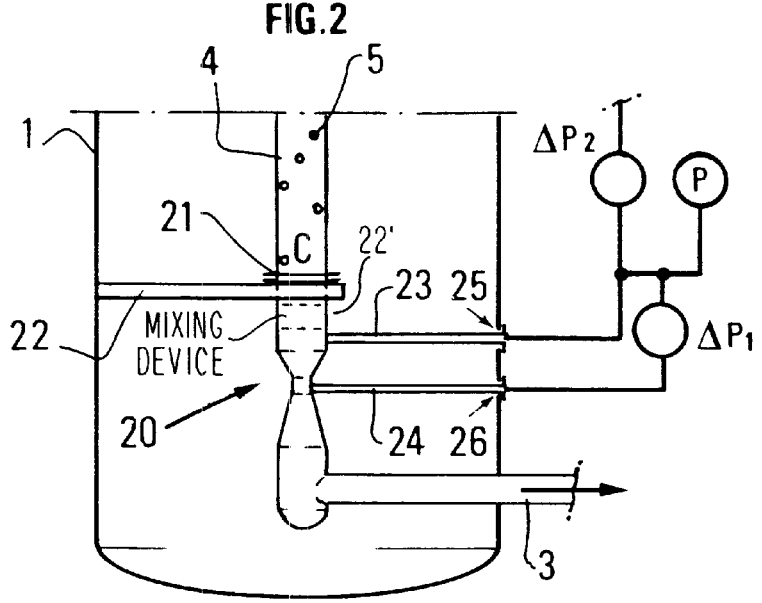

MULTIPHASE FLOW METERING METHOD AND DEVICE

BACKGROUND OF THE INVENTION

1. Field of the Invention

The present invention relates to a method and to a device for determining the value of the flow rate of one or more phases contained in a multiphase effluent, the effluent comprising at least one gas phase and at least one liquid phase.

The invention is used to determine the mass flow rate of the phases of a petroleum effluent comprising a gas phase and a liquid phase (organic and aqueous). The effluent can possibly contain solid particles such as sand, hydrates or paraffins.

The invention is notably applied for enhanced production of a petroleum effluent by injection of gas in the string (gas lift) or by injection of steam in the reservoir. Continuous knowledge of the mass flow rate of the phases produced in each well allows optimum adjustment of the amounts of fluid injected.

2. Description of the Prior Art

Various flow metering methods and devices are known from the prior art.

Patent EP-0 674 249 describes a method and a device allowing mixing of a gas phase and a liquid phase, and to determine the value of the total flow rate of the two phases mixed in a venturi. The method requires a stage of homogenization of the two phases prior to measuring the pressure value at the inlet and at the outlet of the venturi, and a density measuring stage carried out by gammametry, which requires the presence of a radioactive source.

It is well-known to use waves such as microwaves or ultrasonic waves for determining the flow rate of the gas phase and of the liquid phase forming a multiphase effluent. U.S. Pat. Nos. 4,812,739 and 4,820,970 and French Patent 2,722,292 describe methods for determining or measuring, on the one hand, the amount of each of these phases and, on the other hand, an average velocity value or the value of the velocity for each phase, in order to respectively deduce therefrom the average total flow rate or the flow rate of each phase.

The drawback of such devices is that they are expensive and sometimes difficult to install.

SUMMARY OF THE INVENTION

The present invention is a device, flowmeter and a method which overcomes the drawbacks of the prior art.

The present invention relates to a method for determining the value of the flow rate of at least one phase forming a part of a flowing multiphase medium, the multiphase medium comprising at least one liquid phase and at least one gas phase. The invention comprises at least the following steps:

a) feeding the multiphase medium into a chamber comprising at least one delivery line, a sampling device comprising sampling ports and at least one discharge line, b) determining at least two pressure values $P_1$ and $P_2$ at least at two different points A and B of the chamber and/or of the sampling device, and the internal pressure value Po, c) determining, from the values determined in step b), from the knowledge of the density of the gas phase and of the liquid phase and/or from the average value of the density of the multiphase medium in the slotted tube, from a relation connecting at least the following parameters: GLR or the level of the interface between the liquid phase and the gas phase, from pressures $P_1$, $P_2$, Po, the value of the total flow rate Qt of the flowing multiphase medium and/or the flow rate of each of phases $q_g$ and $q_l$.

According to the invention, the value of the flow rate of the gas phase and/or of the liquid phase can be determined by means of relations between the flow rates of the phases and the measured pressure differences, and notably the following relations:

$$q_g = S_g C_g \sqrt{\frac{2(P_1 - P_0)}{g \rho_{0g}}}$$

$$q_l = S_l C_l \sqrt{\frac{2\left(P_2 - P_0 - g\rho_{0l}\frac{z_2}{2}\right)}{g \rho_{0l}}}$$

where $S_g$ and $S_l$ correspond to the sum of the areas of the ports situated in the gas phase and in the liquid phase respectively, $z_2$ being the distance between the liquid-gas interface and a point, $\rho_{og}$ and $\rho_{ol}$ being the densities for the gas and the liquid at the pressure Po and for a temperature $T_o$, $C_g$ and $C_l$ being the values of the passage coefficients of the ports of the slotted tube, and the pressure values $P_1$ and $P_2$ being measured at the level of the sample tube.

$$Qt = q_l + q_g \text{ and } GLR = q_g/q_l.$$

The value of the GLR can be determined by measuring the level of the interface between the gas phase and the liquid phase in the chamber, by taking account of the total height H of the slotted tube and of the characteristics of the sampling device such as the value of the bore coefficient of the tube, the characteristic function of the bore of the slotted tube that equips the chamber f(H,h).

The relation between the various parameters of step c) can be established by calibrating the device by varying the values of the GLR, of the differential pressures Po–$P_1$ and $P_2$–Po and of pressure Po, and of densities ρg, ρl.

The liquid phase has, for example, two liquid phases $L_1$ and $L_2$ of differentiable densities $\rho_1$ and $\rho_2$. A third pressure value $P_3$ is measured in the chamber. The level of the interface between the liquid phase and the gas phase is determined for example by considering the highest liquid level in the chamber, and the value of the fraction of liquid phase $L_1$ is determined, $$W_1 = \frac{1}{\rho_1 - \rho_2}\left[\frac{\rho_3 - \rho_2}{g \times h} - \rho_2\right]$$

$W_1$=fraction of the liquid phase of density $\rho_1$ brought back to volume of the mixture of liquid phases. Stating from the value of $W_1$, it is determined the value of $$x_1 = \frac{W_1}{1 + GLR}$$

corresponding to the fraction of the liquid phase $L_1$, and the value of $$x_2 = \frac{1 - W_1}{1 + GLR}$$

corresponding to the fraction of the liquid phase $L_2$ knowing the value of ql and the values of $x_1$ and/or $x_2$, one determines the value of flowrate $q_{L1}$ and/or $q_{L2}$.

The temperature and/or the pressure prevailing in the chamber can be determined and the density and/or GLR values can be corrected.

The average density $\rho m$ can be determined by measuring the pressure difference between two points located a distance h apart on the slotted tube; the pressure difference can be measured in a flow element situated between the outlet of the slotted tube and the multiphase medium discharge line.

The invention also relates to a device for determining at least the value of the total flow rate of a flowing multiphase medium, the multiphase medium comprising at least one liquid phase and at least one gas phase, the device comprising a chamber provided with at least one delivery line, at least one discharge line and a sampling device comprising sampling ports for removing the liquid phase and the gas phase. The device comprises at least three pressure measuring devices, one intended to measure the internal pressure of the chamber and the two others, the pressure prevailing at two points of the chamber and/or of the sampling device, these point being located a distance d apart, a device which determines the value of the volume ratio GLR of the gas phase and of the liquid phase of the flowing multiphase medium, a processing unit which stores these measured or determined values and initially determined parameter values such as the values of the density of each phase or the average value of the density of the multiphase medium, a relation connecting at least the following parameters: the level of the interface between the gas phase and the liquid phase and/or the GLR, pressure values ($P_1$, $P_2$, Po), the processing unit determining at least the value of the total flow rate Qt of the multiphase medium.

The device can comprise at least one flow element situated between the outlet of the sampling device and the discharge line, the pressure measuring device being placed at the level of the flow element.

The device can comprise a device which determines the average density $\rho m$ of the multiphase medium at the level of the sampling device.

The device can comprise a mixer which mixes the liquid phase and the gas phase, situated between the outlet of the sampling device and the inlet of the flow element.

The device can comprise a filter which filters the solid particles contained in the flowing multiphase medium, the filter being arranged around the slotted tube, and the chamber can have, at least at one end thereof, a shape suited to receive solid particles and a discharge of the solid particles.

The chamber may, for example, be a tube with an inside diameter $\phi int$, the slotted tube having an outside diameter $\phi ext$, the $\phi int/\phi ext$ ratio of the diameters ranging from 1.5 to 5.

The chamber may, for example, be a tube of inside diameter $\phi int$, the slotted tube having an outside diameter $\phi ext$, and the tubes are not coaxial.

The present invention is advantageously used for determining the total flow rate Qt of a petroleum effluent comprising at least one liquid phase and at least one gas phase, and possibly solid particles.

In comparison with the devices of the prior art, the flowmeter according to the invention notably affords the following advantages:

design and operation simplicity, and therefore reduced cost, notably in the absence of densitometric measuring devices using a radioactive source, high reliability, easy installation in places that can be difficult to access, possibility of associating the flow rate measurement with flow control functions within the scope of petroleum production, such as flow rate control or desanding, possibility of estimating the production conditions of each well in real time, and possibly of correcting them automatically by acting on control devices (valves, lift flow rate, steam flow rate, etc.).

BRIEF DESCRIPTION OF THE DRAWINGS

Other features and advantages of the method according to the invention will be clear from reading the description hereafter of a non limitative embodiment example, with reference to the accompanying drawings wherein:

FIG. 1 diagrammatically shows an embodiment of a flowmeter according to the invention, FIG. 2 shows an embodiment of the device of FIG. 1 including a complementary flow element, and FIG. 3 diagrammatically shows a device which discharges for discharging solid particles which may be present in the fluid.

DETAILED DESCRIPTION OF THE INVENTION

Figure 3:
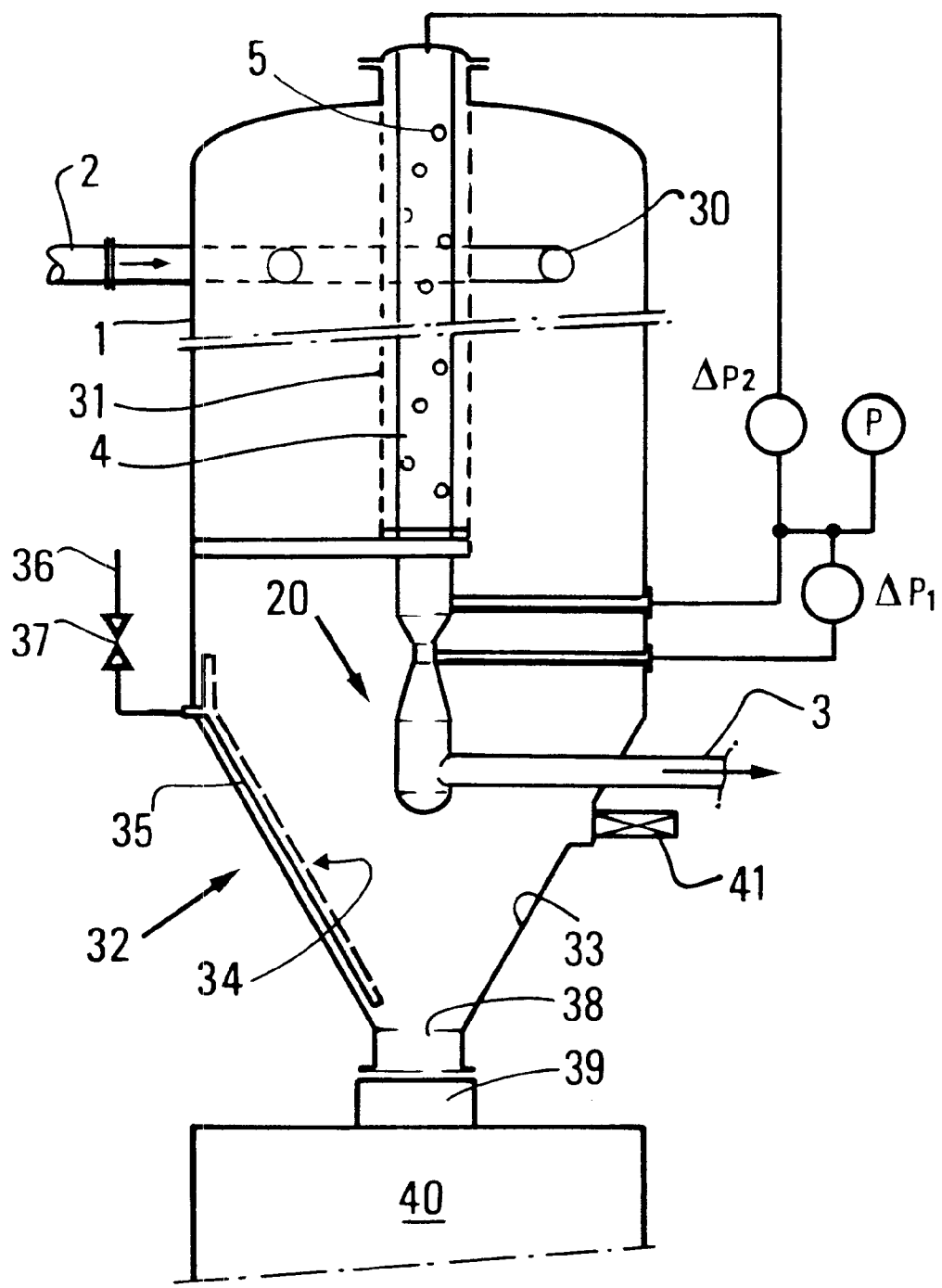

The method according to the invention is implemented by means of a first embodiment given by way of non limitative example and described in FIG. 1.

The object is of the first embodiment is to measure the total flow rate value and/or the flow rate value of each phase of a flowing multiphase medium comprising at least one gas phase and at least one liquid phase. The multiphase medium can be a petroleum effluent comprising a gas phase and a liquid phase generally having an aqueous phase and of an organic phase, and possibly solid particles (sand, hydrate and/or paraffin crystals).

The device or flowmeter comprises a chamber 1 provided with a multiphase effluent delivery line 2, a discharge line 3 and sampling device such as a sample tube 4 having sampling ports 5, the assembly thereof of the tube and the ports hereinafter being referred to as slotted tube. The geometric characteristics of the ports and their distribution along the sample tube can be fixed according to a method described in French Patent 2,685,737 whose technical teaching is incorporated herein by reference.

At least two pressure detectors 6, 7, situated at two different levels A and B of the chamber and/or of the sample tube, as, for example, as illustrated at the bottom and the top when the tube is positioned substantially vertically, measure the pressure values respectively at the outlet of the slotted tube at the level of discharge line 3 and at the opposite end of the slotted tube.

A third pressure detector 8, connected to the wall of the chamber, measures the internal pressure Po of the chamber. An example of layout of the pressure detectors with respect to the slotted tube is given hereafter in FIG. 2.

The flowmeter is equipped with a device which determines the value of the GLR in the chamber, for example a detector 9 which detects the gas phase-liquid phase interface.

A temperature detector 10 measures the real temperature in chamber 1.

The various pressure and temperature detectors and the GLR determination device can be connected to data computing and processing device 11, a microcontroller for example. This microcontroller is capable of storing data specific to the multiphase fluid, for example the density values of each of the gas and liquid phases ρg, ρl, or the average value of the mixture ρm, reference values that are used for data processing, one or more relations H connecting the various measured parameters and the data. The microcontroller is also programmed to deduce the value of the total flow rate Qt of the effluent and/or the value of the flow rate of each phase $q_g$, $q_l$.

The distribution of the ports is for example selected so as to obtain mixing of the phases of the effluent in the slotted tube.

Description of the Method Allowing to Obtain the GLR Value and the Total Flow Rate Value Qt From Three Pressure Measurements, one Being Performed on the Sampling Device $P_0$, $P_1$, $P_2$ a) the average densities of the liquid and gas phases $\rho_{l\,ref}$ and $\rho_{g\,ref}$ are previously determined by measurements on a two-phase fluid sample under known temperature and pressure conditions $T_{ref}$ and $P_{ref}$.

If these densities can evolve on a long-term basis, for example because of the increase in the proportion of water in the liquid phase due to increasing water inflows or, more generally, to variations in the composition of the effluents, the densities are periodically controlled in order to adjust the values considered in the calculation cycle described hereunder. The periodicity of the density measurements can range from several days to several weeks according to the rate of the variations and to the accuracy sought.

b) the pressure $P_0$ in the chamber is measured, as well as possibly the temperature $T_0$ if it varies noticeably with time during the flow rate measurements achieved by means of the present invention. These measurements allow adjustment of the densities measured under the real temperature and pressure conditions prevailing in the chamber in order to obtain densities $\rho_{0l}$ and $\rho_{0g}$. With the gas being assumed to be perfect, the following density is obtained for the gas:

$$\rho_{0g} = \rho_{gref}\frac{P_0}{P_{ref}}\frac{T_{ref}}{T_0}$$

A more accurate law (equation of state) than the gas law can be used in order to improve the accuracy of the method. The degassing of the liquid phase, and possibly the condensation, which causes the gas volume to vary with the pressure drop, can also be taken into account.

The density of the liquid can also be adjusted in order to take account of its thermal expansion and of the degassing by means of known formulas, the effect of compressibility for low pressure variations being generally negligible.

c) the pressure in the slotted tube is measured at least at two points: $P_1$ at a point A preferably situated in the upper part of the tube and $P_2$ at a point B preferably situated in the lower part of the tube, these points being so selected that the interface between the gas phase and the liquid phase(s) remains between A and B.

d) by means of formulas well-known to hydraulic engineers, the gas $q_g$ and liquid $q_l$ flow rates in the ports of the slotted tube are determined from the differences $P_1-P_0$ and $P_2-P_0$, from densities $\rho_{0l}$ and $\rho_{0g}$, and from the geometric and hydraulic characteristics of the ports of the slotted tube: area $S_i$ and bore coefficients $C_i$, which depend on the geometry of the port and on the Reynolds number:

$$q_g = S_g C_g \sqrt{\frac{2(P_1-P_0)}{g\rho_{0g}}}$$

$$q_l = S_l C_l \sqrt{\frac{2(P_2-P_0-g\rho_{0l}\frac{z_2}{2})}{g\rho_{0l}}}$$

$z_2$ being the distance between the (liquid-gas) interface and point B; and $S_g$, $S_l$ the sums of the areas of the ports respectively situated in the gaseous part and in the liquid part. These areas, and therefore the flow rates, depend on the interface level in the chamber:

$$S_g = f_1(h,H),\ S_l = f_2(h,H).$$

e) the densities $\rho_{il}$ and $\rho_{ig}$ and the gas flow rates, possibly the liquid flow rates, at various levels of the slotted tube are corrected in order to take account of the pressure drop $P_1-P_0$ at the top of the tube and $P_2-P_0$ at the bottom, by means of the method described above in step b).

f) the hydrostatic differential pressure and the pressure drops between points A and B are calculated from flow rates $q_g$ and $q_l$.

At point A, we have:

$$\rho_{1g} = \rho_{gref}\frac{P_1}{P_{ref}}\frac{T_{ref}}{T_0} \quad \text{and} \quad q_{1g} = q_g\frac{P_0}{P_1}$$

and at point B:

$$\rho_{2g} = \rho_{gref}\frac{P_2}{P_{ref}}\frac{T_{ref}}{T_0} \quad \text{and} \quad q_{2g} = q_g\frac{P_0}{P_2}.$$

If we disregard the density of the gas, the average density of the two-phase mixture at point B is:

$$\rho_{2aver} = \rho_l\frac{q_l}{q_l+q_{2g}}$$

and the hydrostatic pressure difference is:

$$\Delta P_{hyd} = \frac{1}{2}g\frac{\rho_l q_l}{q_l+q_{2g}}z_2.$$

The pressure drop depends on the square of the calculated total flow rate $Qt=q_{2g}+q_l$ and on the GLR estimated by means of ratio $$\frac{q_{2g}}{q_l},$$

obtained by means of formulas or calculation charts known to specialists. The pressure difference $P_2-P_1$ can therefore be calculated by the expression as follows:

$$(P_2-P_1)_{calculated} = \Delta P_{hyd} - \Delta P_{drop} = \frac{1}{2}g\frac{\rho_l q_l}{q_l+q_{2g}}z_2 - K(q_l+q_{2g})^2$$

where K depends on the flow characteristic and on ratio $$\frac{q_{2g}}{q_l}.$$

This calculated differential pressure depends on the supposed position of the interface.

This calculated value is then compared with the measured pressure difference $P_2-P_1$. This comparison allows modification of the assumed position of the interface and, by means of an iterative approach, to determine the assumed position of the interface which allows good adjustment of the measured pressures to the calculated pressures. When the method has converged it allows obtaining of a level of gas $q_g$ and liquid $q_l$ flow rates, the total flow rate $Qt=q_g+q_l$. The GLR is then determined by means of ratio $$\frac{q_g}{q_l}.$$

Calculation of the flow rates can be made more accurate in several ways. The density of the gas phase can first be taken into account, thus using:

$$\rho_{2aver} = \rho_l \frac{q_l}{q_l + q_{2g}} + \rho_{2g} \frac{q_{2g}}{q_l + q_{2g}}$$

instead of $$\rho_{2aver} = \rho_l \frac{q_l}{q_l + q_{2g}},$$

and this new density is taken into account in all the relations deriving therefrom. Secondly, the slotted tube can be made into several sections and the pressure-flow rate relations of each section can be expressed by adding the partial flow rates from point A to point B. The internal pressure in the tube can be estimated step by step from the pressure $P_1$ measured at point A by means of a relation similar to that mentioned above. In this calculation, the pressure drops in the parts of the tube only filled with gas can be disregarded.

The relations between the measured pressures $P_0$, $P_1$ and $P_2$, the densities $q_g$ and $q_l$, the total flow rate and the GLR and/or the interface level can be analytic type relations stored in a microcomputer with a programmed processing unit. They can also occur as a set of data obtained by means of tests or by calibration of a device and expressed in the form of calculation charts or of a database stored in the microcomputer.

The iterative calculations intended to determine the interface level can be left out if this level is measured. The GLR can be obtained from reading the level by the relation:

$$GLR = \frac{S_g}{S_l} \frac{C_g}{C_l} \sqrt{\frac{P_{0l}}{P_{0g}} \frac{P_1 - P_0}{P_2 - P_0 - P_{g0l}\frac{z_2}{2}}}$$

with $\frac{S_g}{S_l} = f'(h, H)$ (1)

and $C_g$, $C_l$ being bore coefficients of the slotted tube known to those skilled in the art.

Measurements of the temperature and of the pressure prevailing in the chamber can be taken into account in order to correct the GLR value.

Measurements of the temperature prevailing in the chamber and of the pressure values at points A and B or the internal pressure value Po can also be used in order to correct the density values, for example by using the gas law or a more elaborate law selected according to the accuracy sought by the operator.

Po will for example be measured at the level of the effluent delivery line.

For an effluent comprising a mixture of liquid phases that can be differentiated by their density value, it is possible to determine the value of the flow rates of each liquid phase.

For example, when the liquid phase comprises two liquid phases $L_1$ and $L_2$ having respectively densities $\rho_1$, $\rho_2$ and proportions $x_1$ and $x_2$, the proportion of each of these two liquid phases is for example determined and the corresponding flow rate can be obtained as follows:

A third pressure value is determined or measured in the chamber, the measuring point being preferably situated opposite measuring point $P_0$ defined above.

The level of the liquid phase-gas phase interface is determined or measured by taking account of the highest liquid level in the chamber in relation to a low point of the chamber, for example h.

The value of the fraction of the liquid phase $L_1$ is determined, for example with the following steps:

$$W_1 + \frac{1}{\rho_1 - \rho_2}\left[\frac{\rho_3 - \rho_0}{g \times h} - \rho_2\right]$$

$W_1$=fraction of the liquid phase of density $\rho_1$ brought back to the volume of the mixture of the liquid phases, and starting from the value of $W_1$, the following determinations are made: the value of $$x_1 = \frac{W_1}{1 + GLR}$$

corresponding to the fraction of the liquid phase $L_1$, and the value of $$x_2 = \frac{1 - W_1}{1 + GLR}$$

corresponding to the fraction of the liquid phase $L_2$.

From the value of the $q_L$ and the values of $x_1$ and/or $x_2$, one determines the value of flowrate $q_{L1}$ and/or $q_{L2}$ are determined.

FIG. 2 describes another embodiment where a flow element is used in order to measure the pressure difference $\Delta O=P_1-P_2$, for example with a venturi 20 placed directly at the outlet 21 of slotted tube 4. The top portion of FIG. 2 should be understood to be identical to the top portion of FIG. 1.

The flow element can also be a calibrated orifice, a nozzle or any other device suited to measure a pressure drop.

The venturi rests for example on a support 22 with an azimuth index notch. It comprises calibrated recesses allowing insertion of slotted tube 4, discharge line 3 and possibly of pressure measuring tubes 23, 24; the recesses are not shown in the figure for clarity reasons.

Pressure measuring tubes 23, 24 run through openings 25, 26 in chamber 1, which are equipped with suitable seals for the assembly.

In some applications, for example as described in FIG. 3, the slotted tube can also comprise a cup collecting sedimentation of fine sand particles and serving as a damping and anti-abrasion device for the bottom.

The effluent flow in the venturi can be considered as a homogeneous dispersed flow considering the mixture in the perforated tube, and the relation connecting the pressure difference to the velocity of the effluent is as follows:

$$\Delta P = K_2 \rho m\ V^2 \tag{3}$$

$K_2$ is a constant which depends on the geometry of the venturi.

The value of the velocity of flow V of the effluent and therefore the value of its total flow rate Qt in relation to the section of the venturi taken for example at the outlet is determined from the measurement of ΔP between the inlet and the outlet of the venturi, from the value of the average density ρm of the flow and by applying relation (3).

According to another embodiment, the value of the average density ρm is measured by means of the slotted tube placed before the venturi, which notably increases the measuring accuracy.

The pressure value is for example measured at a first point A situated in the upper part of the slotted tube and at a second point C corresponding to the level of the junction of the slotted tube and of the venturi, points A and C lying a distance d apart.

The measured value of ΔP will be connected to an average value of the density ρm by following the method comprising stages a) to f) described above.

The value of the velocity V at the level of the venturi and the value of the total flow rate Qt of the effluent are deduced from the <<measured>> value of ρm, from the measurement of the pressure difference $\Delta P = \Delta P_2$ in the venturi and by applying relation (3).

The pressure and temperature values can be taken into account to correct the value of the GLR, as mentioned above.

Without departing from the scope of the invention, it is possible to position, between the outlet 21 of the slotted tube and the inlet of venturi 20, a device whose purpose is to optimize mixing of the gas phase and of the liquid phase started in the slotted tube prior to their passage into venturi 20 in order to measure the pressure difference. The device can be a venturi. It can be placed inside or outside the chamber.

Without departing from the scope of the invention, it is possible to position, between the outlet 21 of the slotted tube and the inlet of venturi 20, a device 22' whose purpose is to optimize mixing of the gas phase and of the liquid phase started in the slotted tube prior to their passage into venturi 20 in order to measure the pressure difference. The device can be a venturi. It can be placed inside and outside the chamber.

In fact, these particles can form deposits that hinder the effluent flow or damage the inner walls of the transport pipe.

FIG. 3 describes a variant of the device of FIG. 2 equipped with an additional device which separates and filters of the particles before the flow passes into the slotted tube.

The multiphase effluent delivery line 2 can be extended by a tangential inlet 30 so as to create a centrifugal effect. The centrifugal effect tends to drive the solid particles away from slotted tube 4.

The slotted tube is surrounded by a filter 31, for example a 100-micron Johnson type filter, for solid particles having an average size of approximately 200 microns. These filters are conventionally used in the petroleum industry. A stainless metal wire of trapezoid section is wound with a constant pitch leaving a free space between the coils of the required dimension. Passage of fine particles into the slotted tube, which could notably block the sampling ports, is thus minimized.

Chamber 1 can exhibit, in the lower part thereof, a geometry suited to receive the solid particles and to facilitate the discharge thereof, for example a conical shape represented in the figure by a sand cone 32 with an angle α at the apex. The value of angle α can be selected according to the angle of internal friction of the particles or of the sand intended to slide down the inner wall 33 of the chamber without adherence.

Discharge line 3 is preferably placed above the conical part in order to prevent passage of the solid particles.

A fluidization ramp 34 using water injection with tangential jets and provided with ports 35 distributed over most of its length is placed parallel to the conical wall for example. The water is introduced through a line 36 equipped with a valve 37 controlling the rate of the flow injected for example.

The chamber is provided with a solid particles discharge port 38 situated for example at the top of the conical part. The port is connected by a sand valve 39 for example to an external sand tank 40 allowing emptying of the chamber according to controlled sequences for example when the sand level in the chamber reaches a given value. To control these emptying sequences, the chamber comprises a level detector means 41 connected to the microcontroller.

A similar control can possibly carried out in additional tank 40.

Means external to the chamber, such as shakers, to facilitate flow of the particles into the additional tank and possibly to detach them from the walls if need be.

External tank 40 is detachable and it is used, once filled, for transferring the solid deposits to a depollution process unit.

In the various embodiments described above, chamber 1 does not have to provide surge capacity damping of the GLR variations of the effluent, which is unlike the application mentioned in patent French Patent 2,685,737. The inner volume can be reduced and the chamber can be a tube positioned concentrically to the slotted tube. The inside diameter φint of tube 1 is larger than the outside diameter of the slotted tube, the ratio between φext/φint being selected to provide sufficient separation of the liquid and gas phases while reducing the amount of surge effluent.

The φext/φint ratio is therefore preferably selected between 1.5 and 5.0, preferably between 2.0 and 4.0.

The assembly made up of chamber 1 and slotted tube 4 can be positioned with a substantially vertical axis as described in the previous figures or, without departing from the scope of the invention, with an axis inclined to the vertical in order to facilitate separation of the gas phase and of the liquid phase. The inclination can be about 45°.

The axes of the slotted tube and of the tube forming the chamber may not be coaxial.

The distribution of the sampling ports is for example obtained as described in one of the assignee's U.S. Pat. Nos. 5,421,357 or 5,494,067.

The invention can be used for estimating oilwell production conditions and for optimization of reservoir management.

The device according to the invention can be included in a block of wellhead valves usually referred to as Christmas tree in the petroleum industry, for example in subsea applications.

What is claimed is:

1. A method for determining a flow rate value of at least one phase forming a part of a flowing multiphase medium having at least one liquid phase and at least one gas phase, including:

a) feeding the multiphase medium into a chamber having at least one delivery line, a slotted tube having ports through which the multiphase medium flows from the chamber into the tube and out of the slotted tube from at least one discharge line;

b) determining at least two pressure values $P_1$ and $P_2$ at two different points A and B inside the slotted tube with each of two spaced apart pressure sensors which are directly coupled to at least one of the at least one gas and the at least one liquid phase of the flowing multiphase medium, at least one pressure value Po of the chamber and a level of the interface between the liquid phase and the gas phase in the chamber; and c) determining, from the pressure values and the interface level determined at step b), from knowledge of a density $\rho_g$ of the gas phase and a density $\rho_1$ of the liquid phase, from passage coefficients of the ports, at least one of a value of a group comprising a total flow rate Qt, a flow rate $q_1$ of the liquid phase or a flow rate $q_g$ of the gas phase.

2. A method as claimed in claim 1, wherein the total flow rate Qt, the flow rate $q_l$ of the liquid phase and the flow rate $q_g$ of the gas phase are determined by the following relations:

$$Qt = q_l + q_g \text{ and } q_g = S_g C_g \sqrt{\frac{2(P_1 - P_o)}{g\rho_{og}}} \text{ and}$$

$$q_l = S_l C_l \sqrt{\frac{2\left(P_2 - P_o - g\rho_{ol} \frac{z_2}{s}\right)}{g\rho_{ol}}}$$

where $S_g$ and $S_1$ correspond to the sum of the areas of the ports situated respectively in the gas phase and in the liquid phase, $z_2$ is the distance between the liquid-gas interface and the point B, $\rho_{0g}$ and $\rho_{0l}$ are densities for the gas and the liquid at the pressure Po and for a temperature $T_0$, $C_g$ and $C_l$ are passage coefficients of the sampling ports of the slotted tube ports situated respectively in the gas phase and in the liquid phase.

3. A method as claimed in claim 2, wherein the relations Qt and GLR are established by varying at least one value of a group comprising the pressures Po, $P_1$, $P_2$, the level of the interface between the liquid phase and the gas phase, the density $\rho_g$ of the gas phase or the density $\rho_1$ of the liquid phase.

4. An application of the method as claimed in claim 3 comprising:
   determining a total flow rate Qt of a petroleum effluent comprising at least one liquid phase and at least one gas phase.

5. An application of the method as claimed in claim 2 comprising:
   determining a total flow rate Qt of a petroleum effluent comprising at least one liquid phase and at least one gas phase.

6. A method as claimed in claim 1, wherein:
   the liquid phase has two liquid phase $L_1$ and $L_2$ of differentiable densities $\rho_1$ and $\rho_2$, a third pressure $P_3$ is measured in the chamber, the level of the interface between the liquid phase and the gas phase is determined by considering a highest liquid level in the chamber, and a value of a fraction of liquid phase $L_1$ is determined.

7. A method as claimed in claim 6 wherein:
   at least one of a value of a temperature and pressure in the chamber is measured and at least one of the densities $\rho_g$, $\rho 1$, and $\rho_2$ are corrected.

8. An application of the method as claimed in claim 7 comprising:
   determining a total flow rate Qt of a petroleum effluent comprising at least one liquid phase and at least one gas phase.

9. An application of the method as claimed in claim 6 comprising:
   determining a total flow rate Qt of a petroleum effluent comprising at least one liquid phase and at least one gas phase.

10. A method as claimed in claim 1, wherein:
    a value of an average density $\rho m$ is determined by measuring a pressure difference between an inlet and an outlet of a flow element located between the slotted tube and the discharge line.

11. An application of the method as claimed in claim 10 comprising:
    determining a total flow rate Qt of a petroleum effluent comprising at least one liquid phase and at least one gas phase.

12. An application of the method as claimed in claim 1 comprising:
    determining a total flow rate Qt of a petroleum effluent comprising at least one liquid phase and at least one gas phase.

13. A device for determining at least a total flow rate value of a flowing multiphase medium, the multiphase medium having at least one liquid phase and at least one gas phase, the device comprising:
    a chamber having at least one delivery line, a slotted tube having ports through which the multiphase medium flows from the chamber into the tube, and at least one discharge line, at least three pressure measuring sensors, one pressure measuring sensor measuring internal pressure of the chamber and two other pressure measuring sensors each being directly coupled to at least one of the at least one gas phase and the at least one liquid phase of the multiphase flowing medium which respectively measure pressure prevailing at two points of the slotted tube, an interface detector which measures a level of an interface between the liquid phase and the gas phase, a processing device which stores the measured pressures and the interface level which are used by the processing device to determine at least one of a value of a group comprising a total flow rate Qt, a flow rate $q_l$ of the liquid phase or a flow rate $q_g$ of the gas phase.

14. A device as claimed in claim 13, comprising:
    at least one flow element situated between the slotted tube and the discharge line.

15. A device as claimed in claim 14, comprising:
    a mixer which mixes the liquid phase and the gas phase with the mixer being located between an outlet of the slotted tube and the at least one flow element.

16. A device as claimed in claim 15, comprising:
    a filter which traps solid particles contained in the flowing multiphase medium, the filter being disposed around the slotted tube, and the chamber is a shape suited to collect the solid particles and includes a discharge for the solid particles.

17. An application of the device as claimed in claim 16 comprising:

determining a total flow rate Qt of a petroleum effluent comprising at least one liquid phase and at least one gas phase.

18. An application of the device as claimed in claim 15 comprising:

determining a total flow rate Qt of a petroleum effluent comprising at least one liquid phase and at least one gas phase.

19. A device as claimed in claim 14, comprising:

a filter which traps solid particles contained in the flowing multiphase medium, the filter being disposed around the slotted tube, and the chamber is a shape suited to collect the solid particles and includes a discharge for the solid particles.

20. An application of the device as claimed in claim 19 comprising:

determining a total flow rate Qt of a petroleum effluent comprising at least one liquid phase and at least one gas phase.

21. An application of the device as claimed in claim 14 comprising:

determining a total flow rate Qt of a petroleum effluent comprising at least one liquid phase and at least one gas phase.

22. A device as claimed in claim 13, comprising:

means which determines an average density $\rho m$ of the multiphase medium.

23. A device as claimed in claim 22, comprising:

a filter which traps solid particles contained in the flowing multiphase medium, the filter being disposed around the slotted tube, and the chamber is a shape suited to collect the solid particles and includes a discharge for the solid particles.

24. An application of the device as claimed in claim 23 comprising:

determining a total flow rate Qt of a petroleum effluent comprising at least one liquid phase and at least one gas phase.

25. An application of the device as claimed in claim 22 comprising:

determining a total flow rate Qt of a petroleum effluent comprising at least one liquid phase and at least one gas phase.

26. A device as claimed in claim 13, comprising:

a filter which traps solid particles contained in the flowing multiphase medium, the filter being disposed around the slotted tube, and the chamber is a shape suited to collect the solid particles and includes a discharge for the solid particles.

27. An application of the device as claimed in claim 26 comprising:

determining a total flow rate Qt of a petroleum effluent comprising at least one liquid phase and at least one gas phase.

28. A device as claimed in claim 13, wherein:

the chamber has a tube of inside diameter $\phi int$, the slotted rube has an outside diameter $\phi ext$ and a $\phi int/\phi ext$ ratio of the diameters ranging from 1.5 to 5.

29. A device as claimed in claim 28, wherein:

the slotted tube and the tube of inside diameter $\phi int$ are not coaxial.

30. An application of the device as claimed in claim 28 comprising:

determining a total flow rate Qt of a petroleum effluent comprising at least one liquid phase and at least one gas phase.

31. An application of the device as claimed in claim 13 comprising:

determining a total flow rate Qt of a petroleum effluent comprising at least one liquid phase and at least one gas phase.

* * * * *